(12) United States Patent
Riether

(10) Patent No.: US 9,423,411 B2
(45) Date of Patent: Aug. 23, 2016

(54) TRANSPORT DEVICE, SAMPLE DISTRIBUTION SYSTEM AND LABORATORY AUTOMATION SYSTEM

(71) Applicant: Roche Diagnostics Operations, Inc., Indianapolis, IN (US)

(72) Inventor: Christian Riether, Muehltal (DE)

(73) Assignee: Roche Diagnostics Operations, Inc., Indianapolis, IN (US)

(*) Notice: Subject to any disclaimer, the term of this patent is extended or adjusted under 35 U.S.C. 154(b) by 0 days.

(21) Appl. No.: 14/619,409

(22) Filed: Feb. 11, 2015

(65) Prior Publication Data
US 2015/0233957 A1 Aug. 20, 2015

(30) Foreign Application Priority Data
Feb. 17, 2014 (DE) .......................... 10 2014 202 843

(51) Int. Cl.
*G01N 21/00* (2006.01)
*G01N 35/04* (2006.01)

(52) U.S. Cl.
CPC ........ *G01N 35/04* (2013.01); *G01N 2035/0401* (2013.01); *G01N 2035/0465* (2013.01); *G01N 2035/0477* (2013.01)

(58) Field of Classification Search
CPC G01N 35/0098; G01N 35/1081; G01N 35/02
USPC ..................................................... 422/65, 63
See application file for complete search history.

(56) References Cited

U.S. PATENT DOCUMENTS

| | | | |
|---|---|---|---|
| 3,273,727 A | 9/1966 | Rogers et al. |
| 3,653,485 A | 4/1972 | Donlon |
| 3,901,656 A | 8/1975 | Durkos et al. |
| 4,150,666 A | 4/1979 | Brush |
| 4,395,164 A | 7/1983 | Beltrop |
| 4,544,068 A | 10/1985 | Cohen |
| 4,771,237 A | 9/1988 | Daley |
| 5,120,506 A | 6/1992 | Saito et al. |
| 5,295,570 A | 3/1994 | Grecksch et al. |
| 5,309,049 A | 5/1994 | Kawada et al. |
| 5,636,548 A | 6/1997 | Dunn et al. |
| 5,641,054 A | 6/1997 | Mori et al. |
| 5,651,941 A | 7/1997 | Stark et al. |
| 5,720,377 A | 2/1998 | Lapeus et al. |
| 5,735,387 A | 4/1998 | Polaniec et al. |

(Continued)

FOREIGN PATENT DOCUMENTS

| CN | 201045617 Y | 4/2008 |
|---|---|---|
| CN | 10219530 A | 6/2011 |

(Continued)

OTHER PUBLICATIONS

International Search Report issued Sep. 6, 2011 in Application No. PCT/EP2011/057344, 3 pages.

*Primary Examiner* — Natalia Levkovich
(74) *Attorney, Agent, or Firm* — Roche Diagnostics Operations, Inc.

(57) ABSTRACT

A transport device for a sample container is presented. The transport device has a chuck for holding the sample container. The chuck has at least one jaw, which is formed from electrically contractile material. A receiving area for receiving and holding a sample container can thus be enlarged or made smaller. A sample distribution system having such a transport device and a laboratory automation system is also presented.

15 Claims, 2 Drawing Sheets

(56) References Cited

U.S. PATENT DOCUMENTS

| | | |
|---|---|---|
| 5,788,929 A | 8/1998 | Nesti |
| 6,045,319 A | 4/2000 | Uchida et al. |
| 6,062,398 A | 5/2000 | Thalmayr |
| 6,255,614 B1 | 7/2001 | Yamakawa et al. |
| 6,260,360 B1 | 7/2001 | Wheeler |
| 6,279,728 B1 | 8/2001 | Jung et al. |
| 6,429,016 B1 | 8/2002 | McNeil |
| 6,444,171 B1 | 9/2002 | Sakazume et al. |
| 6,571,934 B1 | 6/2003 | Thompson et al. |
| 7,028,831 B2 | 4/2006 | Veiner |
| 7,078,082 B2 | 7/2006 | Adams |
| 7,122,158 B2 | 10/2006 | Itoh |
| 7,278,532 B2 | 10/2007 | Martin |
| 7,326,565 B2 | 2/2008 | Yokoi et al. |
| 7,850,914 B2 | 12/2010 | Veiner et al. |
| 7,858,033 B2 | 12/2010 | Itoh |
| 7,875,254 B2 | 1/2011 | Garton et al. |
| 8,281,888 B2 | 10/2012 | Bergmann |
| 8,796,186 B2 | 8/2014 | Shirazi |
| 9,211,543 B2 | 12/2015 | Ohga et al. |
| 9,239,335 B2 | 1/2016 | Heise et al. |
| 2003/0089581 A1 | 5/2003 | Thompson et al. |
| 2003/0092185 A1 | 5/2003 | Qureshi et al. |
| 2004/0050836 A1 | 3/2004 | Nesbitt et al. |
| 2005/0061622 A1 | 3/2005 | Martin |
| 2005/0109580 A1 | 5/2005 | Thompson |
| 2005/0194333 A1* | 9/2005 | Veiner .................... G01N 35/04 211/74 |
| 2005/0196320 A1 | 9/2005 | Veiner et al. |
| 2005/0226770 A1 | 10/2005 | Allen et al. |
| 2005/0242963 A1 | 11/2005 | Oldham et al. |
| 2005/0271555 A1 | 12/2005 | Itoh |
| 2006/0000296 A1 | 1/2006 | Salter |
| 2006/0047303 A1 | 3/2006 | Ortiz et al. |
| 2007/0116611 A1 | 5/2007 | DeMarco |
| 2007/0210090 A1 | 9/2007 | Sixt et al. |
| 2008/0056328 A1 | 3/2008 | Rund et al. |
| 2008/0131961 A1 | 6/2008 | Crees et al. |
| 2008/0286162 A1 | 11/2008 | Onizawa et al. |
| 2009/0004732 A1 | 1/2009 | LaBarre et al. |
| 2009/0022625 A1 | 1/2009 | Lee et al. |
| 2009/0081771 A1 | 3/2009 | Breidford et al. |
| 2009/0128139 A1 | 5/2009 | Drenth et al. |
| 2009/0142844 A1 | 6/2009 | LeComte |
| 2009/0322486 A1 | 12/2009 | Gerstel |
| 2010/0000250 A1 | 1/2010 | Sixt |
| 2010/0152895 A1 | 6/2010 | Dai |
| 2010/0175943 A1 | 7/2010 | Bergmann |
| 2010/0312379 A1 | 12/2010 | Pedrazzini |
| 2011/0050213 A1 | 3/2011 | Furukawa |
| 2011/0172128 A1 | 7/2011 | Davies et al. |
| 2011/0186406 A1 | 8/2011 | Kraus |
| 2011/0287447 A1 | 11/2011 | Norderhaug |
| 2012/0178170 A1 | 7/2012 | Van Praet |
| 2012/0211645 A1 | 8/2012 | Tullo et al. |
| 2012/0275885 A1 | 11/2012 | Furrer et al. |
| 2012/0282683 A1 | 11/2012 | Mototsu |
| 2012/0310401 A1 | 12/2012 | Shah |
| 2013/0034410 A1 | 2/2013 | Heise et al. |
| 2013/0126302 A1 | 5/2013 | Johns et al. |
| 2013/0153677 A1 | 6/2013 | Leen et al. |
| 2013/0263622 A1 | 10/2013 | Mullen et al. |
| 2013/0322992 A1 | 12/2013 | Pedrazzini |
| 2014/0170023 A1 | 6/2014 | Saito et al. |
| 2014/0231217 A1 | 8/2014 | Denninger et al. |
| 2014/0234065 A1 | 8/2014 | Heise et al. |
| 2014/0234978 A1 | 8/2014 | Heise et al. |
| 2015/0233956 A1 | 8/2015 | Buehr |
| 2015/0276776 A1 | 10/2015 | Riether |
| 2015/0276777 A1 | 10/2015 | Riether |
| 2015/0276778 A1 | 10/2015 | Riether |
| 2015/0276781 A1 | 10/2015 | Riether |
| 2015/0276782 A1 | 10/2015 | Riether |
| 2015/0360876 A1 | 12/2015 | Sinz |
| 2015/0360878 A1 | 12/2015 | Denninger et al. |
| 2016/0003859 A1 | 1/2016 | Wenczel et al. |
| 2016/0069715 A1 | 3/2016 | Sinz |
| 2016/0077120 A1 | 3/2016 | Riether |
| 2016/0097786 A1 | 4/2016 | Malinowski et al. |

FOREIGN PATENT DOCUMENTS

| | | |
|---|---|---|
| DE | 3909786 A1 | 9/1990 |
| DE | 102011090044 A1 | 7/2013 |
| EP | 0601213 A1 | 6/1994 |
| EP | 0775650 A1 | 5/1997 |
| EP | 0896936 A1 | 2/1999 |
| EP | 0916406 A2 | 5/1999 |
| EP | 2148117 A1 | 1/2010 |
| EP | 2327646 A1 | 6/2011 |
| EP | 2447701 A2 | 5/2012 |
| EP | 2502675 A1 | 9/2012 |
| GB | 2165515 A | 4/1966 |
| JP | S56-147209 A | 11/1981 |
| JP | 60-223481 A | 11/1985 |
| JP | 61-081323 A | 4/1986 |
| JP | S61-217434 A | 9/1986 |
| JP | S63-31918 A | 2/1988 |
| JP | S63-48169 A | 2/1988 |
| JP | 01-148966 A | 6/1989 |
| JP | 01-266860 A | 10/1989 |
| JP | H02-87903 A | 3/1990 |
| JP | 3-112393 A | 5/1991 |
| JP | 03-192013 A1 | 8/1991 |
| JP | H05-69350 A | 3/1993 |
| JP | H05-180847 A | 7/1993 |
| JP | 06-026808 A | 4/1994 |
| JP | 06-148198 A | 5/1994 |
| JP | 6-156730 A | 6/1994 |
| JP | 06-211306 A | 8/1994 |
| JP | 07-228345 A | 8/1995 |
| JP | 07-236838 A | 9/1995 |
| JP | H11-083865 A | 3/1999 |
| JP | H11-264828 A | 9/1999 |
| JP | H11-304812 A | 11/1999 |
| JP | H11-326336 A | 11/1999 |
| JP | 2000-105243 A | 4/2000 |
| JP | 2000-105246 A | 4/2000 |
| JP | 2001-124786 A1 | 5/2001 |
| JP | 2001-240245 A | 9/2001 |
| JP | 2005-249740 A | 9/2005 |
| JP | 2006-106008 A | 4/2006 |
| JP | 2007-309675 A1 | 11/2007 |
| JP | 2007-314262 A | 12/2007 |
| JP | 2007-322289 A | 12/2007 |
| JP | 2009-145188 A | 7/2009 |
| JP | 2009-300402 A | 12/2009 |
| JP | 2013-172009 A | 9/2013 |
| JP | 2013-190400 A | 9/2013 |
| SU | 685591 A1 | 9/1979 |
| WO | 96/36437 A1 | 11/1996 |
| WO | 2003/042048 A3 | 5/2003 |
| WO | 2007/024540 A1 | 3/2007 |
| WO | 2008/133708 A1 | 11/2008 |
| WO | 2009/002358 A1 | 12/2008 |
| WO | 2010/042722 A1 | 4/2010 |
| WO | 2010/087303 A1 | 8/2010 |
| WO | 2010/129715 A1 | 11/2010 |
| WO | 2011/138448 A1 | 11/2011 |
| WO | 2012/158520 A1 | 11/2012 |
| WO | 2012/158541 A1 | 11/2012 |
| WO | 2013/169778 A1 | 11/2013 |
| WO | 2014/059134 A1 | 4/2014 |

* cited by examiner

TRANSPORT DEVICE, SAMPLE DISTRIBUTION SYSTEM AND LABORATORY AUTOMATION SYSTEM

CROSS-REFERENCE TO RELATED APPLICATIONS

This application claims priority to DE 10 2014 202 843.4 filed Feb. 17, 2014, which is hereby incorporated by reference.

BACKGROUND

The present disclosure generally relates to a transport device and, in particular, to a transport device for receiving and fixing a sample container and for transporting the sample container, a sample distribution system and a laboratory automation system.

Sample containers are typically elongate vessels, which are open on one side, are usually made of transparent glass or plastic, and which are used to store and to transport mostly liquid samples. Samples of this type are blood samples, for example.

There is a need to provide a transport device, a sample distribution system and a laboratory automation system that can be easily handled.

SUMMARY

According to the present disclosure, a transport device for receiving and fixing a sample container and for transporting the sample container between pre-analytical, analytical and/or post-analytical stations of a laboratory automation system is presented. The transport device can comprise at least one magnetically active element. The at least one magnetically active element can interact with a magnetic field such that a driving force can be applied to the transport device. The magnetic field can be generated by at least one electromagnetic actuator. The transport device can further comprise a holding unit comprising a chuck having a plurality of jaws. The plurality of jaws can extend radially inwardly from an outer edge. A receiving area for the sample container can be formed between the plurality of jaws. At least one jaw of the plurality of jaws can be formed from an electrically contractile material and can be electrically contacted in such a way that a control voltage and/or a control current can be applied to the electrically contractile material. The at least one jaw formed from electrically contractile material can contract radially outwardly thereby expanding the receiving area when the control current and/or the control voltage is applied.

In accordance with one embodiment of the present disclosure, a sample distribution system is presented that can utilize the transport device.

In accordance with another embodiment of the present disclosure, a laboratory automation system is presented that can utilize the sample distribution system.

Accordingly, it is a feature of the embodiments of the present disclosure to provide a transport device, a sample distribution system and a laboratory automation system that can be easily handled. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
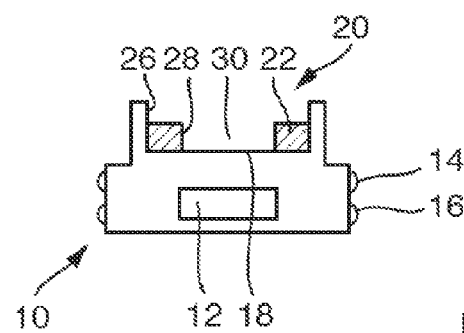
FIG. 1 illustrates schematically a sectional view from the side of a transport device according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A transport device for receiving (holding, including, collecting) and fixing a sample container, in particular in the form of a sample tube, is presented. The transport device can further be used to transport the sample container between pre-analytical, analytical and/or post-analytical stations of a laboratory automation system. The transport device may be a sample carrier, for example. A pre-analytical station can usually be used for the preliminary processing of samples or sample containers. An analytical station can be designed, for example, to use a sample or part of the sample and a reagent in order to produce a measurable signal, on the basis of which it is possible to determine whether the analyte is present, and if so in what concentration. A post-analytical station can usually be used for the post-processing of samples or sample containers.

The pre-analytical, analytical and post-analytical stations may comprise, for example, at least one station from the group of following stations: a cap removal station for removing caps or closures on sample tubes, a cap fitting station for fitting caps or closures on sample tubes, an aliquoting station for aliquoting samples, a centrifuging station for centrifuging samples, an archiving station for archiving samples, a pipetting station for pipetting, a sorting station for sorting samples or sample tubes, a sample tube type determination station for determining a sample tube type, and a sample quality determination station for determining a sample quality The transport device can have at least one magnetically active element, for example in the form of one or more permanent magnets and/or in the form of ferromagnetic material. The magnetic element can interact with a magnetic field, which can be generated by at least one electromagnetic actuator, in such a way that a driving force can be applied to the transport device and/or the magnetically active element. The transport device can further have a holding unit for receiving and detachably fixing a sample container.

The holding unit can have a chuck or a receiving apparatus or holding apparatus having one or more jaws, that is to say a plurality of jaws can be at least one. The jaw or jaws can extend radially inwardly from an outer, circular edge. A receiving area for a sample container can be defined or formed between the jaw or the jaws. The jaw or at least one jaw of the jaws can be formed from an electrically contractile material and can be electrically contacted in such a way that the electrically contractile material can be acted on by a control voltage and/or a control current in such a way that the jaw or jaws formed from electrically contractile material can contract radially outwardly with expansion of the receiving area when acted on by the control current and/or the control voltage. The outer edge can also be formed in particular as a physical delimitation of the holding unit and/or the transport device. By way of example, it may be a peripheral ring.

By way of example, the receiving area can also be referred to as an insertion area or can be used as such. Here, a sample container can be slid in the longitudinal direction or longitudinal extension thereof into the receiving area. The receiving area may be the area in which a sample container is typically received. The receiving area can be precisely of such a size that it can be slightly smaller than a diameter of the sample container in the case that no jaw is contracted and no sample container is located in the receiving area. The sample container can thus be held between the jaws with slight pressure due to elastic deformation, provided no control current and/or no control voltage is applied. It may also be said that the receiving area or insertion area can be provided or can be formed between the jaws.

A control voltage or a control current can be applied, for example, in such a way that a defined voltage can be applied or a defined current can be conveyed through the electrically contractile material by a voltage source or a current source, respectively.

It is possible, by the transport device, to transport a sample container with use of magnetic fields on a transport surface. Furthermore, the embodiment of the chuck can enable a simple release and fixing of a sample container, such that it can be received in and removed from the transport device easily in an automated manner. To this end, merely the switching on and off, respectively, of a control current and/or a control voltage is necessary.

The electrically contractile material can also be used as an actuator for other types of clamping jaws, that is to say the electrically contractile material, for example, can push/press rubber blocks against the sample container or influences the angle of mechanical levers.

In accordance with one embodiment, all jaws of the chuck can be formed from electrically contractile material and can be electrically contacted. The respective jaws can contract radially outwardly with expansion of the receiving area when acted on by the control current and/or the control voltage. In this case, the jaws can contract radially outwardly uniformly. A uniform expansion of the receiving area can thus be achieved, which can simplify the handling and provide more space for accommodation and/or removal of a sample container.

In accordance with one embodiment, the chuck can have one individual jaw formed as a ring. Alternatively, the chuck can have two, three, four, five or six separate jaws, for example. It can be understood that suitable numbers of jaws may be advantageous for different sample containers and different purposes.

The electrically contractile material may be an electroactive polymer, a gel, an electroactive polymer, a magnetoactive polymer, a gel of a magnetoactive polymer, or a material that demonstrates a piezoelectric effect. Here, a gel can be understood in particular to be a finely dispersed system formed of at least one solid and one liquid phase. Electrically contractile materials for example can be polyacrylonitrile-polypyrrole (PAN-PPY), polyvinyl alcohol (PVA), polyvinylidene fluoride (PVDS), an acryl material or a gel formed from such materials.

The jaws can be formed from electrically contractile material, each can be electrically contacted by two electrodes. At least one electrode can be peripheral, such that it can contact a plurality of jaws at the same time. An identical reference potential can thus be produced in a simple manner for a plurality of jaws.

The transport device may have a first and a second electrical contact area. The first and the second electrical contact area can be electrically contacted with the jaws formed from electrically contractile material. The first and the second electrical contact area can be formed on the outer side or peripheral side of the transport device. This can enable a simple contacting by suitable apparatuses, for example, electrodes for contacting the electrical contact areas at suitable points, which for example can be provided for loading and unloading of the transport device.

The first and the second electrical contact area may be formed as electrically conductive strips running horizontally around the transport device. The first electrical contact area can be distanced from the second electrical contact area in the vertical direction. This can enable an electrical contacting of the electrical contact areas independently of the present orientation of the transport device.

In accordance with one embodiment, at least the jaws formed from an electrically contractile material can be coated with a layer of silicone. This may then be advantageous if the electrically contractile material itself cannot be cleaned or can only be cleaned with difficulty. The silicone layer, specifically in this case, can allow a simple cleaning of the respective jaw and can prevent an infiltration of water or other cleaning fluid into the electrically contractile material. It can be understood that a respective jaw can be coated wholly or partially with the layer made of silicone.

A sample distribution system is also presented. The sample distribution system can comprise the following: a plurality of transport devices, a planar horizontally oriented transport surface to carry the transport devices, a plurality of electromagnetic actuators arranged in a stationary manner below the transport surface, wherein the electromagnetic actuators can move a transport device arranged on the transport surface, by exerting a magnetic force onto the transport device, and a control device to activate the electromagnetic actuators in such a way that it can move a transport device on the transport surface along a predefinable transport path.

By the sample distribution system, the advantages mentioned above for the transport device can be used for a sample distribution system. In terms of the transport device, reference can be made to all further embodiments described above. Explained advantages can apply accordingly.

The control device may be, for example, a computer, a processor or another electronic control apparatus. The control device may comprise processor and storage. A program code controlling the behavior of the processor can be stored in the storage.

The sample distribution system may comprise a handling station, activated by the control device, for loading and/or unloading a transport device. The handling station can have a first and a second electrical contact, which can be used to produce an electrical connection to the transport device or the first and second electrical contact area thereof. The handling station can further comprise a gripper, which can be used to handle a sample container received or to be received in the transport device.

By the electrical contacts of the handling station, corresponding electrical contact areas of the transport device can be electrically contacted. By way of example, these may be the peripheral contact areas described above. In this case, it may be sufficient to provide one narrow stationary contact for contacting a respective peripheral contact area on the transport device. This may simplify handling, in particular in the case of a round transport device, since the radial orientation of the transport device does not have to be taken into consideration.

A sample container can be inserted into a transport device in a simple fully automated manner. Due to the expanded receiving area, which can be produced by the control voltage and/or the control current and the electrically contractile material, the insertion of the sample container by the gripper can be facilitated. Tolerances can thus be compensated for more easily. The sample container can then be held reliably in the transport device by simply switching off the control voltage and/or the control current.

The transport device can be rotationally symmetrical. This can allow a simple production and can further avoid a preferred direction, such that the transport device can be moved two-dimensionally on the transport surface with use of magnetic fields without having to take into account a momentary orientation of the transport device.

In accordance with one embodiment, a sample container of which the diameter can be greater than a diameter of the receiving area without applied current flow can be received in a transport device. The sample container can thus be held suitably in the transport device under slight pressure due to elastic deformation of the jaws, which for example can prevent the sample container from accidentally falling out or tipping over.

To unload a sample container, the control device can move to the handling station, the transport device in which the sample container to be unloaded can be received, by activating the electromagnetic actuators, to activate the gripper in such a way that the sample container can be held by the gripper, to apply a control voltage and/or a control current to the at least one jaw of the transport device formed from electrically contractile material, such that this can widen the receiving area, and lastly to activate the gripper in such a way that the sample container can be removed from the transport device and, for example, can be fed to a pre-analytical, analytical and/or post-analytical station for further treatment/processing.

To load a sample container, the control device can move to the handling station, a transport device that is to be loaded with a sample container, by activating the electromagnetic actuators, to apply a control voltage and/or a control current to the at least one jaw of the transport device formed from electrically contractile material, such that this can widen the receiving area, to activate the gripper in such a way that the sample container can be introduced along the longitudinal extension thereof by the gripper into the receiving area, to deactivate the control voltage and/or the control current, such that the receiving area of the transport device narrows, and lastly to activate the gripper in such a way that it can release the sample container, such that the transport device can be moved on the transport surface.

A laboratory automation system can have a number of pre-analytical, analytical and/or post-analytical stations, which can process sample containers and/or samples contained in the sample containers, and an above-mentioned sample distribution system for transporting the sample containers between the pre-analytical, analytical and/or post-analytical stations.

Figure 2:
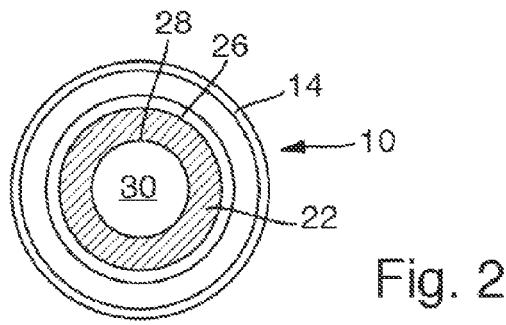
FIG. 2 illustrates schematically a plan view of the transport device from FIG. 1 according to an embodiment of the present disclosure.

Referring initially to FIGS. 1 and 2, a transport device 10 is shown. FIG. 1 shows a sectional view from the side, whereas FIG. 2 shows a plan view of the transport device 10. The transport device 10 can be radially symmetrical. It can have approximately the form of a puck. On the underside thereof, the transport device can be flat, such that it can rest on and slide over a transport surface in a suitable manner.

A magnetically active element in the form of a permanent magnet 12, which can make it possible to move the transport device 10 through an external magnetic field on the transport surface, can be located in the transport device 10.

A first electrical contact area 14 and a second electrical contact area 16, which can be formed as peripheral electrically conductive strips, can be located laterally on the transport device 10. This can enable a peripheral contacting of the electrical contact areas 14, 16 independently of angle of rotation.

A recess 18 can be provided on an upper side of the transport device 10. A chuck 20 can be located in the recess 18 and can be provided to receive and hold a sample container. The chuck 20 can have a radially peripheral jaw 22. This can be formed from electrically contractile material. A radially peripheral first electrode 26 can be arranged radially outside the jaw 22. This first electrode can contact the jaw 22 from outside. Within the jaw 22, there can be a second electrode 28, which can likewise be radially peripheral and which can contact the electrically contractile material of the jaw 22 from inside.

The first electrode 26 can be connected to the first electrical contact area 14. The second electrode 28 can be connected to the second electrical contact area 16. This can make it possible to apply a voltage and/or to produce a current between the electrodes 26, 28, which voltage/current can be applied to or flows through the jaw 22 radially.

A receiving area 30 can be formed within the jaw 22 into which receiving area a sample container can be introduced. The receiving area 30 can be so large here that, in a state in which no current and no voltage are produced, it can be slightly smaller than a diameter of a sample container to be received. The jaw 22 can thus exert a radial fixing force onto a received sample container due to elastic deformation, the fixing force preventing an accidental removal or tipping over. The interface between the jaw 22 and the receiving area 30 can be coated with silicone in order to enable improved cleaning.

If a voltage is applied to the electrical contact areas 14, 16 from outside, the electrically contractile material of the jaw 22 can contract. This can enlarge the receiving area 30. Such a state can be used, for example, in order to load the transport device 10 with a sample container or in order to remove the sample container.

Figure 3:
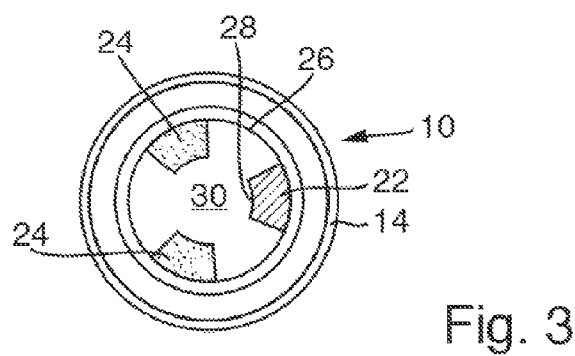
FIG. 3 illustrates schematically a plan view of a transport device according to another embodiment of the present disclosure.

FIG. 3 shows a further exemplary embodiment, in which not only an individual jaw 22 made of electrically contractile material is provided, but additionally two further jaws 24 can also be provided, which comprise non-electrically contractile material. The three jaws 22, 24 can be arranged in a manner rotated by about 120° relative to one another over the shape of a circle and each can occupy one segment of a circular arc. The jaw 22 can comprise of electrically contractile material that does not run all the way around.

By applying a voltage or a current, as described with reference to FIGS. 1 and 2, the jaw 22 comprising electrically contractile material can contract and thus can enlarge the receiving area 30. This can lead, in spite of the constant form of the two jaws 24 not comprising electrically contractile material, to the possibility of a facilitated introduction or removal of a sample container.

Figure 4:
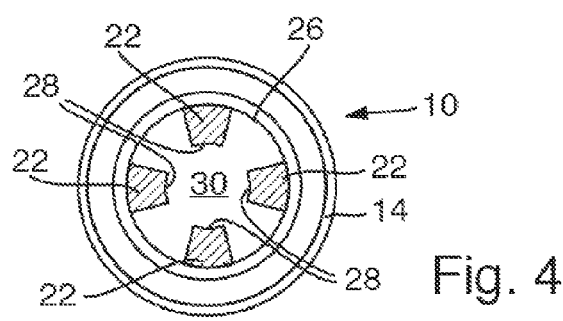
FIG. 4 illustrates schematically a plan view of a transport device according to a further embodiment of the present disclosure.

FIG. 4 shows a further embodiment of a transport device 10. The transport device 10 according to FIG. 4 can have a total of four jaws 22, each made of electrically contractile material. Each jaw 22 can be electrically contacted by a first electrode 26 running peripherally on the outer side and by a respective inner second electrode 28 associated with the receiving area 30.

When an electric voltage or an electric current is applied to the jaws 22, they can contract uniformly. This can enlarge the receiving area 30 uniformly. More space for loading and unloading the transport device 10 can thus be made available advantageously.

Figure 5:
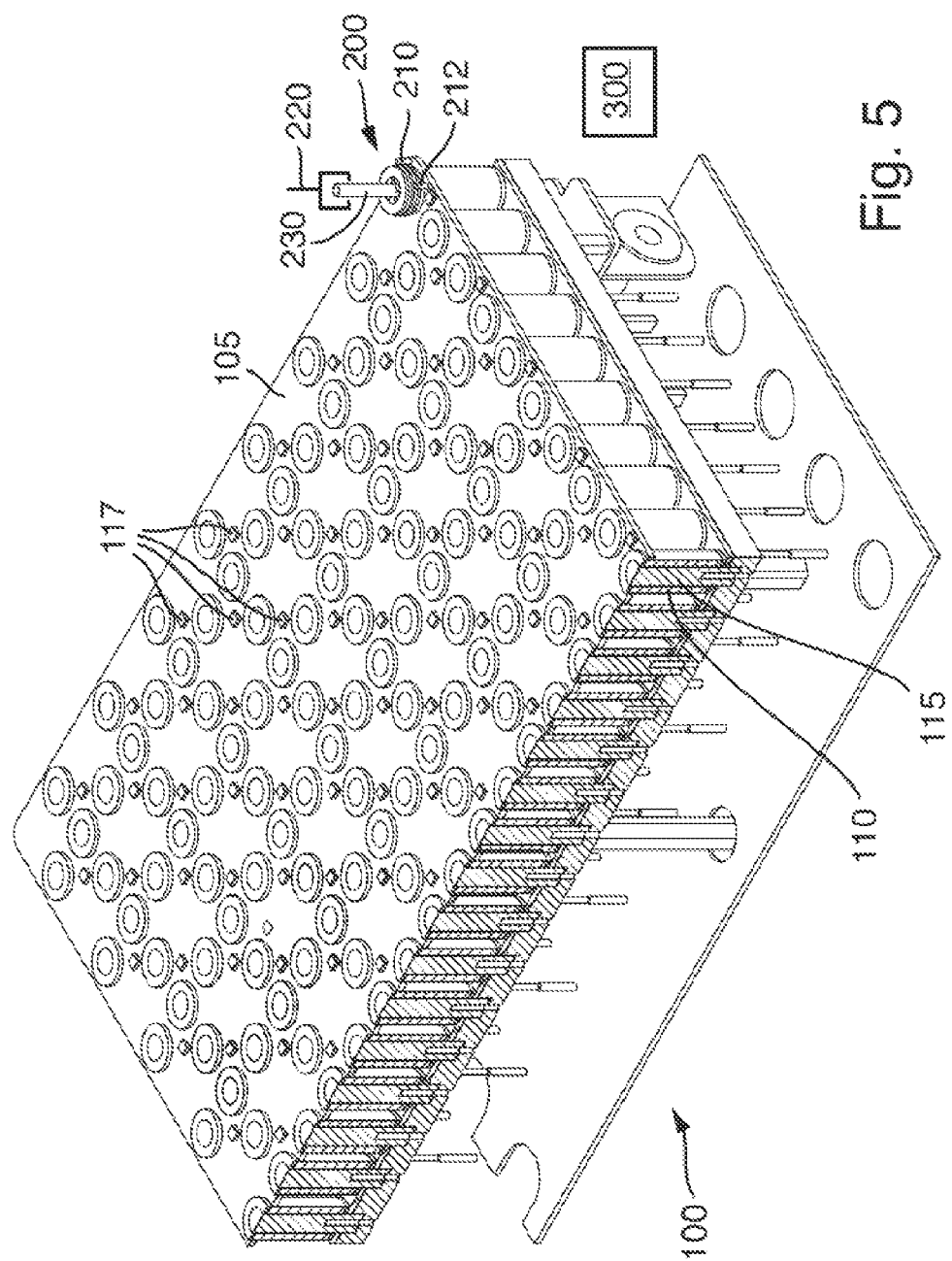
FIG. 5 illustrates schematically a sample distribution system according to an embodiment of the present disclosure.

FIG. 5 shows a sample distribution system 100. The sample distribution system 100 can have a transport surface 105, on which transport devices 10 can be moved. A plurality of electromagnets 110 with ferromagnetic cores 115 can be located below the transport surface 105. These electromagnets can be actuated individually by a control device 300, such that a transport device 10 can be moved over the transport surface 105 along a predefined path by the permanent magnets 12 of the transport device on account of the magnetic fields generated by the coils 110. In order to determine the respective position of a transport device 10, a number of Hall sensors 117 can be additionally arranged on the surface 105. The Hall sensors can detect the magnetic field generated by the permanent magnets 12 and can communicate the corresponding position of the transport device 10 to the control device 300.

The sample distribution system 100 can be part of a laboratory automation system having a plurality of pre-analytical, analytical and post-analytical stations, which can be arranged adjacently to the transport surface 105. The sample distribution system 100 can used be to transport the sample containers between these stations.

The sample distribution system 100 can further have a handling station 200 for loading and unloading a transport device 10. The handling station 200 can have a first stationary electrical contact 210 and a second stationary electrical contact 212. The stationary electrical contacts 210, 212 can be provided in a corner region of the transport surface 105 and can serve simultaneously as a stop for a transport device 10. Here, the first electrical contact 210 can be arranged at such a height that it can contact the first electrical contact area 14 in the case in which a transport device 10 can be located in the station 200. The second stationary electrical contact 212 can be arranged such that it can contact the second electrical contact area 16 in the case in which a transport device 10 can be located in the handling station 200. Since the electrical contact areas 14, 16 can be formed peripherally, the position of rotation of the transport device 10 may be irrelevant.

The handling station 200 can further have a gripper 220 to introduce a sample container 230 into a receiving area 30 of a transport device 10 or to remove a sample container therefrom. This can enable an automated loading and unloading of a transport device 10 with a sample container 230.

The control device 300 can guide a transport device 10 to the handling station 200. The transport device 10 can be loaded or unloaded by the electromagnetic actuators 110. There, the transport device can be held by the electromagnetic actuator 110 located below the station 200. The control device 300 can then apply a voltage by the stationary electrical contacts 210, 212 to the jaws 22 of the transport device 10 formed from electrically contractile material. The receiving area 30 can thus expand, and the control device 300 can actuate the gripper 220 in order to insert/remove a sample container 230 into/from the transport device 10.

By the shown sample distribution system, loading and unloading processes and also transport processes can be carried out with simple equipment set-up and fully automatically. Time and costs can thus be saved, and operating errors can be avoided.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

I claim:

1. A transport device for receiving and fixing a sample container and for transporting the sample container between pre-analytical, analytical and/or post-analytical stations of a laboratory automation system, the transport device comprising:
    at least one magnetically active element, wherein the at least one magnetically active element interacts with a magnetic field such that a driving force is applied to the transport device and wherein the magnetic field is generated by at least one electromagnetic actuator; and
    a holding unit comprising a chuck having a plurality of jaws;
    wherein the plurality of jaws extend radially inwardly from an outer edge of the holding unit, wherein a receiving area for the sample container is formed between the plurality of jaws, wherein at least one jaw of the plurality of jaws is formed from an electrically contractile material, wherein a first electrode contacts outside the electrically contractile material of the at least one jaw and a second electrode contacts inside the electrically contractile material of the at least one jaw, wherein the first electrode is connected to a first electrical contact area and the second electrode is connected to a second electrical contact area, wherein the first and second electrical contact areas are located laterally on the transport device, and wherein the at least one jaw formed from electrically contractile material contracts radially outwardly thereby expanding the receiving area when a control current and/or a control voltage is applied to the first electrical contact area and the second electrical contact area.

2. The transport device according to claim 1, wherein the plurality of jaws of the chuck are formed from electrically contractile material and are electrically contacted.

3. The transport device according to claim 2, wherein the plurality of jaws of the chuck contract radially outwardly thereby expanding the receiving area when the control current and/or the control voltage is applied.

4. The transport device according to claim 1, wherein the chuck has a plurality of two, three, four, five or six jaws which forms a ring.

5. The transport device according to claim 1, wherein the chuck is comprised only of the at least one jaw which forms a ring.

6. The transport device according to claim 1, wherein the electrically contractile material is an electroactive polymer, a gel of an electroactive polymer, a magnetoactive polymer, a gel of a magnetoactive polymer, or a material that demonstrates a piezoelectric effect.

7. The transport device according to claim 1, wherein the electrically contractile material is polyacrylonitrile-polypyrrole (PAN-PPY), polyvinyl alcohol (PVA), polyvinylidene fluoride (PVDS), an acryl material or a gel formed from such materials.

8. The transport device according to claim 1, further comprising
a first and a second electrical contact area, wherein the first and the second electrical contact area are electrically connected to the at least one jaw formed from electrically contractile material.

9. The transport device according to claim 8, wherein the first and the second electrical contact area are formed as electrically conductive strips running horizontally around the transport device.

10. A sample distribution system, the sample distribution system comprising:
a plurality of transport devices according to claim 1;
a transport surface to carry the transport devices;
a plurality of electromagnetic actuators, wherein the plurality of electromagnetic actuators are arranged in a stationary manner below the transport surface, wherein the electromagnetic actuators move a transport device arranged on the transport surface by applying a magnetic force to the transport device;
a plurality of surface sensors on the transport surface that detect position of the plurality of transport devices generated by the at least one magnetically active element of the plurality of transport devices; and
a control device in communication with the plurality of electromagnetic actuators and the plurality of surface sensors, the control device having a processor and storage, wherein the control device activates the electromagnetic actuators so that the electromagnetic actuators apply the magnetic force to the transport device such that the transport device moves on the transport surface along a predefinable movement path and wherein the plurality of surface sensors communicate the position of the plurality of transport devices to the control device.

11. The sample distribution system according to claim 10, further comprising
a handling station activated by the control device for loading and/or unloading a transport device.

12. The sample distribution system according to claim 11, wherein the handling station comprises a first and a second electrical contact for establishing an electrical connection to the transport device and a gripper for handling a sample container received or to be received in the transport device.

13. The sample distribution system according to claim 12, wherein the control device:
moves a transport device, in which a sample container to be unloaded is received, to the handling station by activation of the electromagnetic actuators;
activates the gripper in such a way that the sample container is held by the gripper;
applies a control voltage and/or a control current to the first electrical contact area and the second electrical contact area connected to the first electrode and second electrode of the at least one jaw of the transport device formed from electrically contractile material; and
activates the gripper in such a way that the sample container is removed from the transport device.

14. The sample distribution system according to claim 12, wherein the control device:
moves a transport device, which is to be loaded with a sample container, to the handling station by activation of the electromagnetic actuators;
applies a control voltage and/or a control current to the first electrical contact area and the second electrical contact area connected to the first electrode and second electrode of the at least one jaw of the transport device formed from electrically contractile material;
activates the gripper in such a way that the sample container is introduced by the gripper into the receiving area;
deactivates the control voltage and/or the control current; and
activates the gripper in such a way that this releases the sample container.

15. A laboratory automation system, the laboratory automation system comprising:
a plurality of pre-analytical, analytical and/or post-analytical stations to process sample containers and/or samples contained in the sample containers; and
a sample distribution system for transporting the sample containers between the pre-analytical, analytical and/or post-analytical stations according to claim 10.

* * * * *